United States Patent
Temmler et al.

(10) Patent No.: US 7,152,461 B2
(45) Date of Patent: Dec. 26, 2006

(54) METHOD AND APPARATUS FOR DETERMINATION OF THE DEPTH OF DEPRESSIONS WHICH ARE FORMED IN A MOUNT SUBSTRATE

(75) Inventors: Dietmar Temmler, Dresden (DE); Peter Weidner, Rötz (DE)

(73) Assignee: Infineon Technologies AG, Munich (DE)

( * ) Notice: Subject to any disclaimer, the term of this patent is extended or adjusted under 35 U.S.C. 154(b) by 56 days.

(21) Appl. No.: 11/060,571

(22) Filed: Feb. 17, 2005

(65) Prior Publication Data
US 2005/0199078 A1 Sep. 15, 2005

(30) Foreign Application Priority Data
Feb. 18, 2004 (DE) .................... 10 2004 007 952

(51) Int. Cl.
*G01B 5/28* (2006.01)
(52) U.S. Cl. .................... 73/105; 73/104; 73/866
(58) Field of Classification Search ............ 73/104, 73/105, 38, 866
See application file for complete search history.

(56) References Cited

U.S. PATENT DOCUMENTS

| | | | |
|---|---|---|---|
| 3,605,501 A * | 9/1971 | Chenevert .................... | 73/866 |
| 5,321,634 A | 6/1994 | Obata et al. | |
| 5,625,170 A | 4/1997 | Poris | |
| 6,194,234 B1 * | 2/2001 | Huang et al. .................. | 438/14 |
| 6,284,986 B1 | 9/2001 | Dietze et al. | |
| 6,306,545 B1 * | 10/2001 | Carlson et al. ............. | 429/247 |
| 6,684,685 B1 * | 2/2004 | Gupta et al. ................... | 73/38 |
| 6,708,559 B1 * | 3/2004 | Chen et al. .................. | 73/149 |
| 7,020,577 B1 * | 3/2006 | Wilby ........................ | 702/713 |
| 2003/0061890 A1 | 4/2003 | Chen et al. | |

FOREIGN PATENT DOCUMENTS

WO WO-02/03449 A2 1/2002

* cited by examiner

Primary Examiner—Michael Cygan
(74) Attorney, Agent, or Firm—Morrison & Foerster LLP

(57) ABSTRACT

The invention relates to a method for determination of the depth of depressions which are formed in a mount substrate. According to the invention, an essentially uniform layer of a wetting agent is applied, which contains depressions, on a surface of the mount substrate, a time profile of the decrease in weight of the mount substrate is recorded, and the recorded time profile of the decrease in weight of the mount substrate is evaluated. The invention also relates to a measurement apparatus.

20 Claims, 6 Drawing Sheets

METHOD AND APPARATUS FOR DETERMINATION OF THE DEPTH OF DEPRESSIONS WHICH ARE FORMED IN A MOUNT SUBSTRATE

CLAIM FOR PRIORITY

This application claims priority to German Application No. 10 2004 007 952.8 filed Feb. 18, 2004, which is incorporated herein, in its entirety, by reference.

TECHNICAL FIELD OF THE INVENTION

The present invention relates to a method and an apparatus for determination of the depth of depressions which are formed in a mount substrate.

BACKGROUND OF THE INVENTION

Nowadays, the electronics for microelectronic semiconductor components are dominated by integrated circuits. These integrated circuits are formed from a complex arrangement of electronic structures which are connected to one another in a number of levels, arranged one above the other, on a semiconductor mount which is referred to as a chip. The joint production of chips on a semiconductor wafer is characterized by a complicated sequence of different process steps.

The main objective of the semiconductor industry is continuous performance improvement by means of ever faster circuits while at the same time further miniaturizing the electronic structures. In the course of this development process, there has been an increasing trend towards three-dimensional structures for the production of chips on semiconductor wafers, with the advantage of reducing the space required on the surfaces of the semiconductor wafers. In general, depressions or trenches which are formed in the semiconductor wafers act as the original structures for such three-dimensional structures, and are etched into the surfaces of the semiconductor wafers and/or into layers applied to the surfaces of the semiconductor wafers.

The miniaturization of the electronic structures is linked to more stringent requirements for the precision of the production processes that are used. At the same time, precision inspection methods are required in order to monitor the production processes. With regard to three-dimensional structures, accurate determination of the depth of depressions formed in the semiconductor wafers is, in particular, of major importance since this parameter can have a considerable influence on the functionality of the chips.

At present atomic force microscopes are preferably used to determine the depth of depressions formed in the semiconductor wafers, based on the use of a measurement probe to scan the surface to be investigated. The interaction processes (Van der Waal bonding forces) which occur as the probe mechanically approaches the surface, can thus be used to obtain surface information. This allows the depth of depressions to be measured with high accuracy of approximately 1 nanometer. Owing to the continuous miniaturization of the structures, the depressions to be measured are, however, becoming ever narrower, thus resulting in more stringent requirements for the geometry, the robustness and the resistance to wear of the measurement probes that are used, as well as more stringent requirements for the scanning process. This is particularly true of structures and depressions with a high aspect ratio, that is to say a high ratio of the depth to the lateral size. Depth determination by means of atomic force microscopes is thus becoming ever more costly and complex. Furthermore, the measurement times are increasing, thus reducing the throughput of measurable semiconductor wafers.

Alternatively, scanning electron microscopes can be used to determine the depth of depressions. In this case, the semiconductor wafer to be investigated is broken in the area of the depressions and a scanning electron microscope is used to record the fracture edge. However, this method is costly and tedious owing to the need to break the semiconductor wafer. Furthermore, the semiconductor wafer is destroyed by breaking it so that the method is highly costly and is suitable only for off-line measurement of only a small proportion of the semiconductor wafers.

3D scanning electron microscopes can be used for non-destructive determination of depths, in which a scanning electron microscope is used to record a surface and at least two different tilt angles. These records are then correlated with one another in order to calculate a 3D data record. This data record can be used to obtain cross-sectional information, and thus to determine the depth of depressions. The very long measurement times have been found to be a major disadvantage of this method. Furthermore, the depth determination becomes increasingly inaccurate as the aspect ratio of the depressions increases.

WO 02/03449 A2 discloses a method and a measurement apparatus for determination of the thickness of layers formed on semiconductor wafers. This is done by measuring the weight of the semiconductor wafer before and after the deposition of a layer, by means of a weighing device. The layer thickness or else the density of the layer can then be deduced from the difference between the recorded weight values. Even a large-area or structured deposited layer, deposited, for example, by means of an etching process, can be recorded by means of this differential weighing method. However, it has the disadvantage that two independent weight measurements are carried out, that is to say before and after the deposition process or etching process. Since, on the one hand, errors from these two independent measurements may be superimposed and, on the other hand, drift may occur in the weighing device between the two measurements, the accuracy of the measurement method is limited. Furthermore, only a representative mean value can be determined for the parameter of interest, such as the layer thickness, and this does not allow any statement to be made about its local distribution.

SUMMARY OF THE INVENTION

The present invention provides an improved method and an improved apparatus, by means of which the depth of depressions formed in a mount substrate can be determined non-destructively, quickly and with high accuracy.

According to one embodiment of the invention, there is a method for determination of the depth of depressions which are formed in a mount substrate, in which, in a first method step, an essentially uniform layer of a wetting agent is applied to an area, which includes depressions, on a surface of the mount substrate, filling the depressions, a time profile of the decrease in weight of the mount substrate during the vaporization of the wetting agent is recorded in a second method step, and the recorded time profile of the decrease in weight of the mount substrate is evaluated in a third method step in order to determine a characteristic weight value for the mount substrate in a state in which the wetting agent has vaporized from the surface of the mount substrate and the depressions are still completely filled with the wetting agent.

The depth of the depressions is then determined, in a fourth method step, from the characteristic weight value taking into account the intrinsic weight value of the mount substrate without the wetting agent, the density of the wetting agent and the total surface area occupied by the depressions in the area of the surface of the mount substrate.

The invention is advantageous by making it possible to easily and quickly determine the depth of depressions formed in a mount substrate, with high accuracy. Since the method does not involve destruction of the mount substrate, the method is cost-effective. Furthermore, the method can be used without any problems for determination of the depth of depressions with a high aspect ratio. In addition, it is possible to determine the depth of depressions in a locally limited area of the surface of the mount substrate provided that this area is wetted.

The characteristic weight value of the mount substrate, which reflects a state of the mount substrate, in which the wetting agent is vaporized from the surface of the mount substrate, in contrast the depressions are (still) completely filled with the wetting agent represents one theoretical weight value. This weight value is passed through during a vaporization process which takes place in ideal conditions and in which the surface is completely uniformly wetted. In order to determine the characteristic weight value from a time profile of the decrease in weight of the mount substrate recorded in real conditions, one particularly preferred embodiment makes use of the fact that the characteristic weight value corresponds to the intersection of a first straight line which is defined by a first linear section of the recorded time profile of the decrease in weight and a second straight line which is defined by a second linear section of the recorded time profile. In this case, the first linear section of the recorded time profile corresponds to a state of the mount substrate in which the wetting agent has vaporized from the entire area of the surface of the mount substrate, and the second linear section of the recorded time profile corresponds to a state of the mount substrate in which the wetting agent has vaporized exclusively from the depressions but none of the depressions have yet been completely emptied.

In another embodiment of the invention, the wetting agent is applied as drops of a predetermined size to the surface of the mount substrate in order to form a predetermined circular wetted area. The total area occupied by the depressions in the wetted area can be deduced from the number of depressions located in the predetermined wetted area and from the area occupied by a depression in the surface of the mount substrate. The size of the wetted area can in this case be recorded accurately by additionally measuring the wetted area using an imaging method.

According to a preferred embodiment, the intrinsic weight value of the mount substrate is determined before or after the recording of the time profile of the decrease in weight of the mount substrate during the vaporization of the wetting agent. The method is very accurate because the intrinsic weight value for the two alternatives and the time profile of the decrease in weight are recorded with little time separation, since, by way of example, measurement errors which can result from drifting of a weighing device that is used for the weight measurements are avoided.

It is also preferable for the mount substrate to be raised to a predetermined temperature value in order to produce a predetermined vaporization rate of the wetting agent.

In another preferred embodiment, the surface of the mount substrate is cleaned and dried before the application of the wetting agent, in order to achieve complete, bubble-free wetting of the surface of the mount substrate and in the depressions. This further improves the accuracy of the method.

Complete, bubble-free wetting of the surface of the mount substrate and in the depressions can also be achieved, according to a further preferred embodiment, by using a wetting agent with a defined viscosity and affinity.

Furthermore, according to yet another embodiment of the invention, an apparatus is proposed for determination of the depth of depressions which are formed in a mount substrate having a metering device for application of an essentially uniform layer of a wetting agent to an area, which includes depressions, on a surface of the mount substrate, having a weighing device for recording a time profile of the decrease in weight of the mount substrate during the vaporization of the wetting agent and for determination of the intrinsic weight value of the mount substrate without the wetting agent, and having an evaluation device for evaluation of the recorded time profile of the decrease in weight of the mount substrate in order to determine a characteristic weight value for the mount substrate in a state in which the wetting agent has vaporized from the surface of the mount substrate and the depressions from the characteristic weight value taking into account the intrinsic weight value of the mount substrate without the wetting agent, the density of the wetting agent and the total surface area occupied by the depressions in the area of the surface of the mount substrate.

The apparatus according to the invention accordingly allows the depth of depressions formed in a mount substrate to be determined highly accurately, easily, quickly and non-destructively.

BRIEF DESCRIPTION OF THE INVENTION

The invention will be explained in more detail in the following text with reference to the figures, in which.

DETAILED DESCRIPTION OF THE INVENTION

Figure 1:
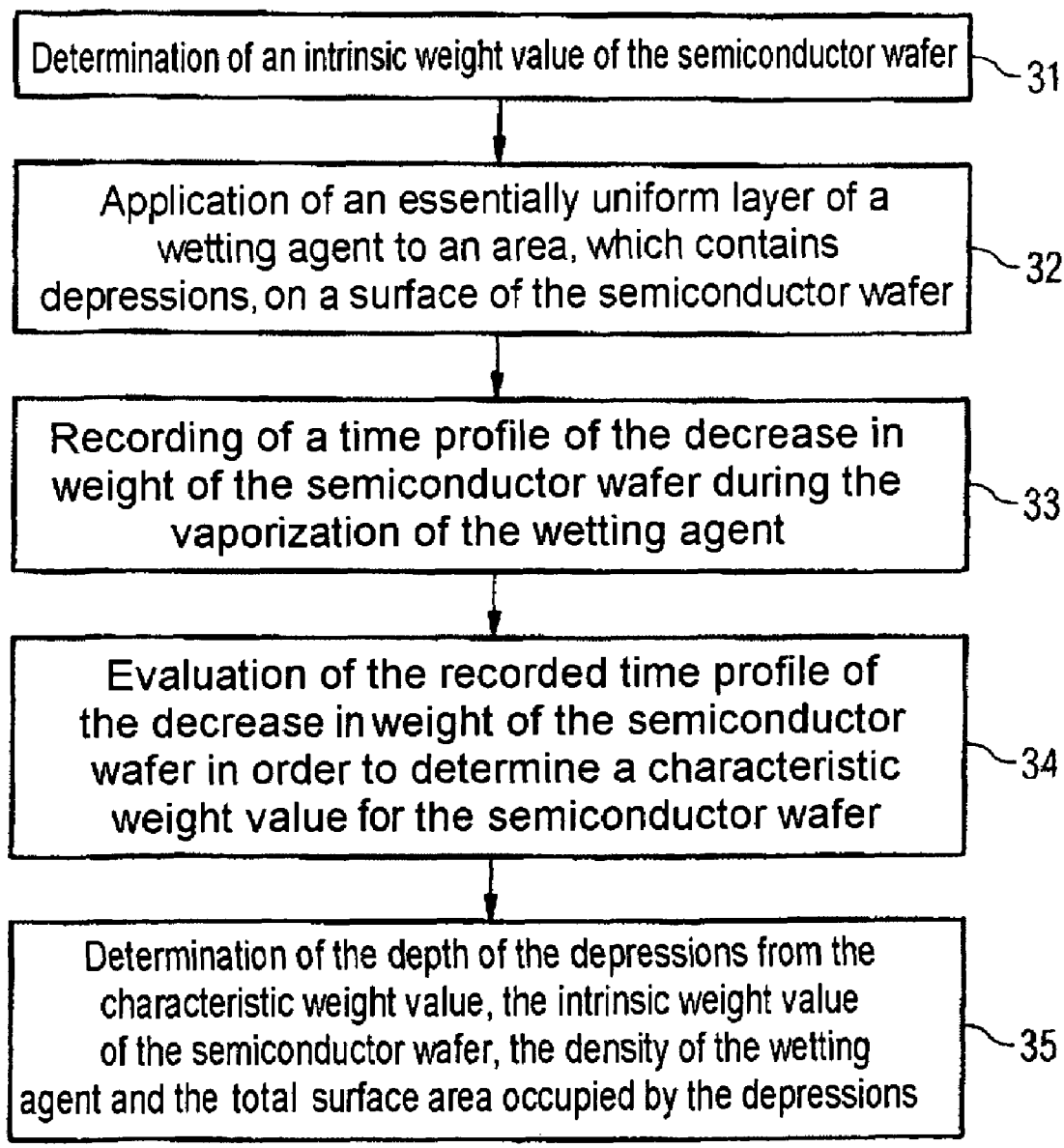
FIG. 1 shows a flowchart of one embodiment of the method according to the invention for determination of the depth of depressions which are formed in a semiconductor wafer.

FIG. 1 shows a flowchart of one embodiment of the method according to the invention for determination of the depth of depressions which are formed in a semiconductor wafer. In this case, an intrinsic weight value of the semiconductor wafer is determined in a first method step 31, after which an essentially uniform layer of a wetting agent is applied in a method step 32 to an area including depressions on a surface of the semiconductor wafer with the depressions being filled, and a time profile of the decrease in weight of the semiconductor wafer during the vaporization of the wetting agent is recorded in a subsequent method step 33. The recorded time profile of the decrease in weight of the semiconductor wafer is then evaluated in a method step 34 in order to determine a characteristic weight value for the semiconductor wafer. This characteristic weight value for the semiconductor wafer corresponds to a state in which the wetting agent has vaporized from the surface of the semiconductor wafer and the depressions are (still) completely filled with the wetting agent. The depth of the depressions is then determined in a method step 35 from the characteristic weight value, the intrinsic weight value of the semiconductor wafer without the wetting agent, the density of the wetting agent and the total area occupied by the depressions in the area of the surface of the semiconductor wafer.

Figure 2:
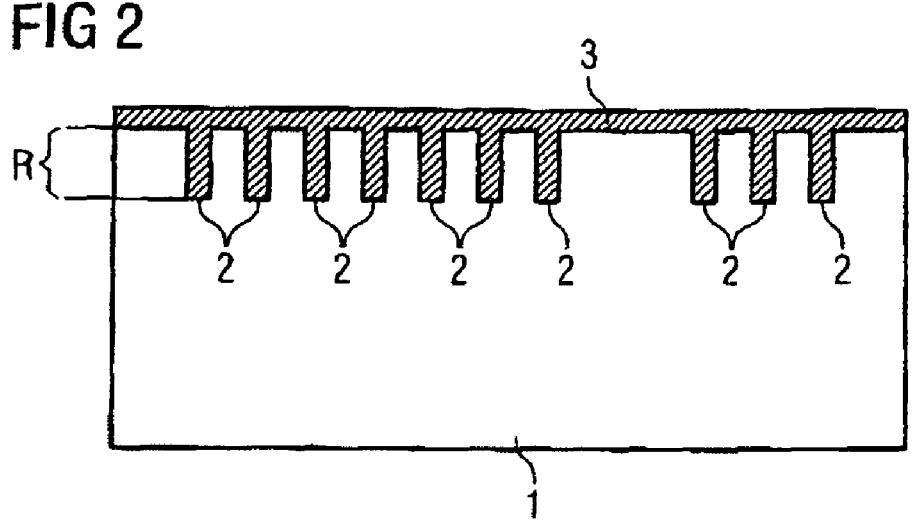
FIGS. 2 to 4 show schematic section illustrations of a semiconductor wafer having depressions formed in its upper face during the process of vaporization of a wetting agent which has been applied to the semiconductor wafer.
Figure 3:
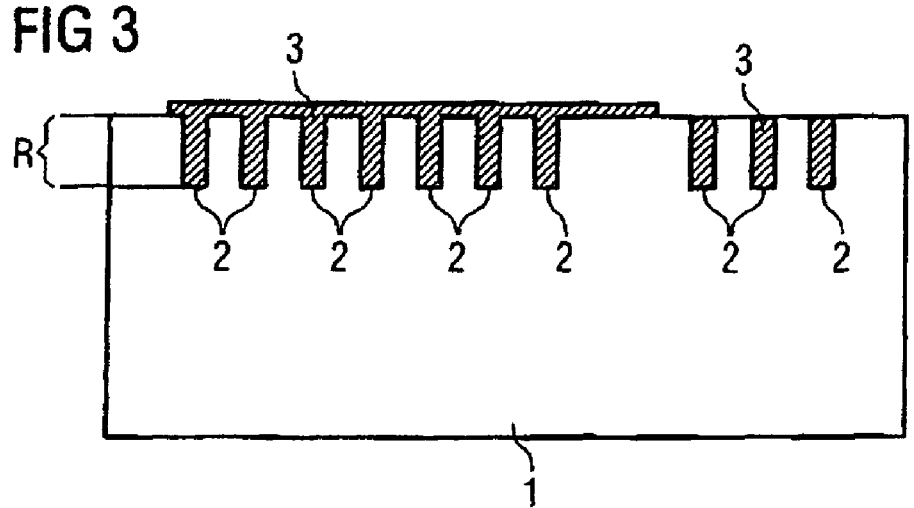
Figure 4:
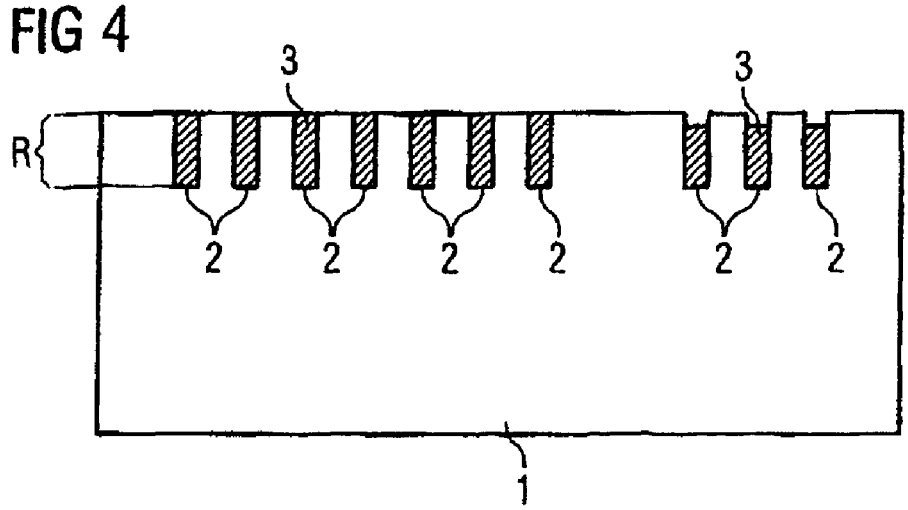

The method according to the invention will be explained in more detail with reference to the following figures. FIGS. 2 to 4 show schematic section illustrations of a detail of a semiconductor wafer 1 having depressions 2 formed in its upper face during the process of vaporization of a wetting agent 3 which has been applied to a semiconductor wafer 1. The depressions 2 which, by way of example, represent trenches etched in its upper face of the semiconductor wafer 1 for trench capacitors of a DRAM memory chip, have a depth R which can be determined quickly and highly accurately by means of the method according to the invention as illustrated in FIG. 1.

FIG. 2 shows the semiconductor wafer 1 at a time immediately after the application of the wetting agent 3 to that area of the surface of the semiconductor wafer 1 which includes the illustrated depressions 2. The wetting agent 3 is in this case preferably applied as droplets of a predetermined size to the surface of the semiconductor wafer 1 in order to form a predetermined circular wetted area. By way of example, a metering nozzle is used for application of the wetting agent.

As illustrated in FIG. 2, the area of the surface of the semiconductor wafer 1 to be investigated is covered with an essentially uniform and closed layer or a film of the wetting agent 3. The wetting agent 3 vaporizes from the entire wetted surface of the semiconductor wafer 1 at a constant vaporization rate. In consequence, the thickness of the layer formed from the wetting agent 3 and thus also the weight of the semiconductor wafer 1 decrease linearly in proportion to time. This time period for the decrease in weight of the semiconductor wafer 1 is referred to in the following text as phase I.

As the vaporization process continues, the layer formed from the wetting agent 3 becomes ever thinner. Since this layer never covers the semiconductor wafer 1 exactly uniformly in practical conditions, individual subareas of the semiconductor wafer 1 are not covered by the wetting agent 3 in this case, as is illustrated in FIG. 3. The time period which is referred to in the following text as phase II then starts, in which increasingly planar subareas of the surface of the semiconductor wafer 1 are exposed. The exposed subareas now contribute to the decrease in weight of the semiconductor wafer 1 by vaporization from the depressions 2 which are located in these subareas.

Thus, in comparison to phase I the decrease in weight of the semiconductor wafer 1 slows down in phase II until the entire surface of the semiconductor wafer 1 is exposed, and the wetting agent 3 then vaporizes from the depressions 2.

This time, which marks the start of the subsequent section of the decrease in weight of the semiconductor wafer 1 that is referred to in the following text as phase III, is illustrated in FIG. 4. Phase III is once again characterized by a constant vaporization rate of the wetting agent 3, and thus by the weight of the semiconductor wafer 1 decreasing in proportion to time. In comparison to phase I, the linear decrease in weight of the semiconductor wafer 1 in phase III takes place, however, with a longer time constant, since the wetting agent 3 vaporizes only from the depressions 2.

Phase III of the time profile continues until individual depressions 2 have been completely emptied. In the time period which starts at this point and is referred to as phase IV, the number of completely empty depressions 2 increases, so that the decrease in weight of the semiconductor wafer 1 becomes continuously slower. As soon as the wetting agent 3 has vaporized from the last depression 2, the semiconductor wafer 1 once again has its intrinsic weight value.

In order to achieve preferred wetting, which is as complete and bubble-free as possible, of the surface of the semiconductor wafer 1 and in the depressions, it is advantageous to carry out the method using a wetting agent 3 having a defined viscosity and affinity which produce complete and bubble-free wetting. In addition, it is possible to clean and to dry the surface of the semiconductor wafer 1 before the application of the wetting agent 3, and before the determination of the intrinsic weight value of the semiconductor wafer 1.

A chemically inert wetting agent 3 is preferably used in order to avoid chemical reactions between the wetting agent 3 and the semiconductor wafer 1. With regard to the semiconductor manufacture and to further method steps which are carried out on the semiconductor wafer 1 provided with depressions 2, it is also advantageous to use a high-purity wetting agent 3 which is compatible with the process. The purity and process compatibility of the wetting agent 3 can be ensured in particular by the use of a purity level which has already been introduced for semiconductor manufacture and which is appropriate for the substance used. By way of example, thinners of photoresists or alcohol may be used. Optionally, the process compatibility can also be assisted by additional cleaning of the semiconductor wafer 1 after the time profile of the decrease in weight of the semiconductor wafer 1 has been recorded.

Furthermore, an explosion-proof wetting agent 3 which is not hazardous to health is preferably used. The wetting agent 3 has, in particular, a vaporization rate which is advantageous for the recording of the time profile of the decrease in weight of the semiconductor wafer 1.

A vaporization rate predetermined in this way for the wetting agent 13 can also be achieved by raising or lowering the semiconductor wafer 1 to a predetermined temperature value. This temperature value is preferably in the room temperature range.

Figure 5:
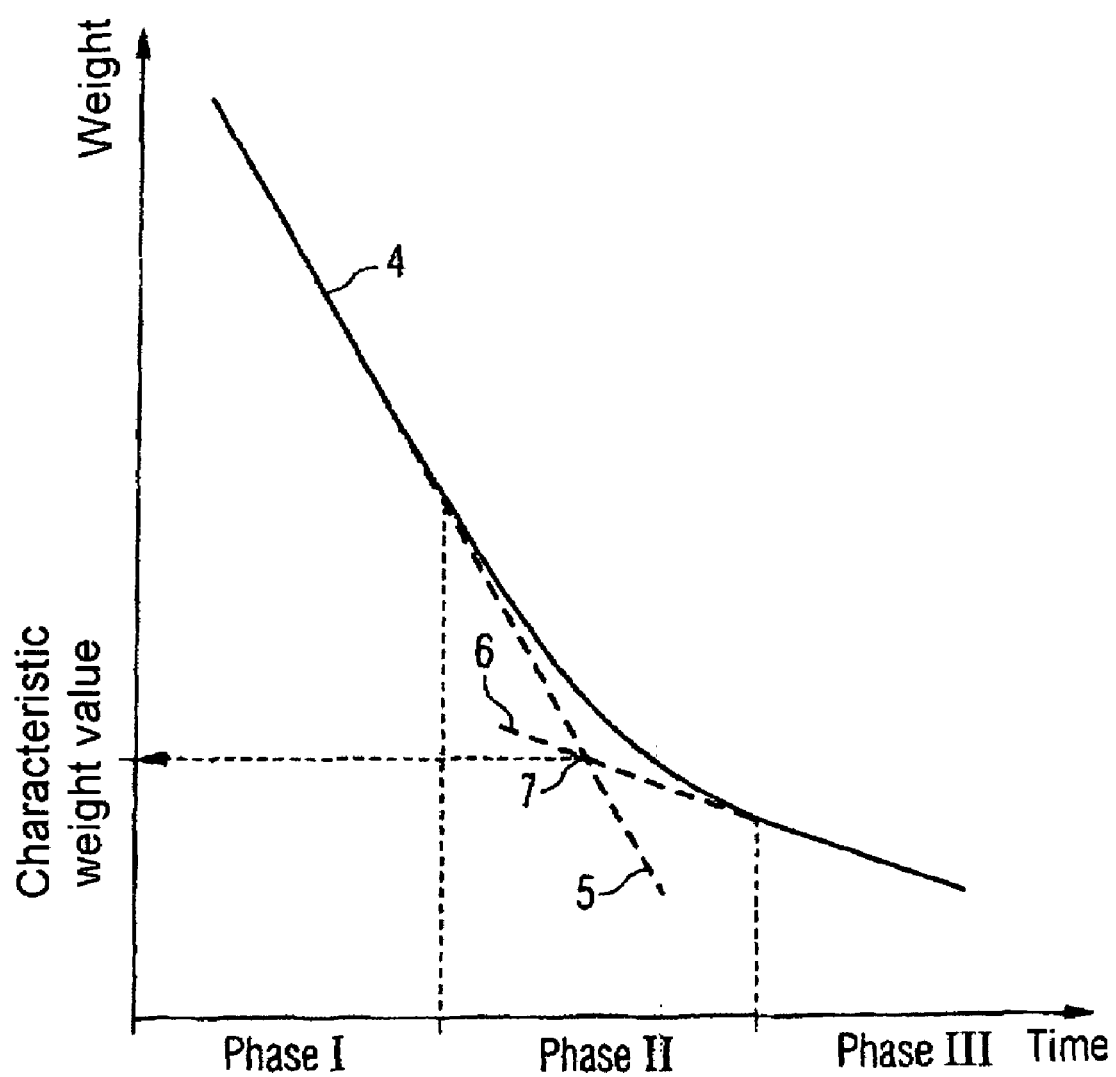
FIG. 5 shows a schematic illustration of a recorded time profile of the decrease in weight of the semiconductor wafer during the vaporization of the wetting agent.

FIG. 5 shows a schematic illustration of a recorded time profile 4 of the decrease in weight of the semiconductor wafer during the vaporization of the wetting agent. This clearly shows the various phases in the time profile 4 that have been explained with reference to the previous FIGS. 2 to 4. In phase I, in which the wetting agent is vaporizing from the entire area of the surface of the semiconductor wafer, the weight of the semiconductor wafer decreases linearly. In phase II, the decrease in weight slows down, since more and more subareas of the surface have been exposed by the vaporization of the wetting agent. In phase III, in which the wetting agent is vaporizing exclusively from the depressions, the decrease in weight has a linear profile again, but with a longer time constant than in phase I. The subsequent phase IV, in which the decrease in weight of the semiconductor wafer becomes continuously slower until the semiconductor wafer has reached its intrinsic weight value, is actually not illustrated in the time profile 4 shown in FIG. 5.

The sought characteristic weight value corresponds to a (theoretical) state of the semiconductor wafer in which the wetting agent has vaporized from the surface of the semiconductor wafer and all the depressions are completely filled with the wetting agent. This weight value is passed through only during a vaporization process taking place in ideal conditions, in which the surface is always wetted completely uniformly, and which therefore does not occur explicitly in the recorded time profile 4.

The characteristic weight value is in consequence determined on the basis of a theoretical profile which approximates to the recorded profile 4 and reflects the ideal vaporization process. In the ideal vaporization process, phase I merges smoothly into phase III and there is no phase II. The theoretical profile based on the ideal vaporization profile can in consequence be reproduced with the aid of two straight lines 5, 6, which each approximate to the linear sections of the time profile 4 in the phases I and III, respectively. The intersection 7 of these straight lines 5, 6 then corresponds to the sought characteristic weight value of the semiconductor wafer in the (theoretical) state in which the wetting agent has vaporized from the surface of the semiconductor wafer and the depressions are still completely filled with the wetting agent.

The depth of the depressions can then be determined from the characteristic weight value of the semiconductor wafer obtained in this way, from its intrinsic weight value without the wetting agent, from the density of the wetting agent, and from the total area occupied by the depressions in the area of the surface of the semiconductor wafer. These parameters are related to the depth R in accordance with the equation:

$$R = \frac{\Delta m}{D_N \times A}$$

where $\Delta m$ corresponds to the difference between the characteristic weight value and the intrinsic weight value of the semiconductor wafer, and thus to the weight of the wetting agent in the completely filled depressions, $D_N$ corresponds to the density of the wetting agent and A corresponds to the total area occupied by the depressions.

In order to precisely determine the total area occupied by the depressions, the wetted area after the application of the wetting agent is measured in the method according to the invention as illustrated in FIG. 1. This is done using an imaging method and an image recording device. The total area occupied by the depressions in the wetted area can be deduced from the number of depressions located in the predetermined wetted area and from the known area occupied by a single depression on the surface of the semiconductor wafer.

Furthermore, it may be advantageous to observe and/or to measure the wetted area of the surface of the semiconductor wafer throughout the entire vaporization process. This makes it possible to monitor the wetting of the surface of the semiconductor wafer in the various phases of the vaporization process.

It is also possible to record the concentration of the vaporized wetting agent during the vaporization process by means of appropriate sensor devices. This allows the vaporization process to be monitored, and the various phases to be assessed.

Since the method according to the invention as illustrated in FIG. 1 does not involve destruction of the semiconductor wafer, the method is particularly suitable for in-line measurement of the depth of depressions formed in product wafers.

It is also particularly advantageous that the depth of depressions in a small, locally limited area of the surface of the semiconductor wafer can be determined by means of the method according to the invention. Only this area need be wetted for this purpose. The minimum size of a locally limited wetted area such as this is in this case governed by the measurement accuracy of the weighing device that is used to record the decrease in weight of the semiconductor wafer. The local distribution of the depth can be recorded by carrying out the method a number of times on a number of locally limited areas.

Instead of applying the wetting agent to only one subarea of the surface of the semiconductor wafer for the method according to the invention, it is also possible to apply the wetting agent to the entire surface of the semiconductor wafer containing depressions, preferably excluding the wafer edge. This makes it possible to obtain a mean value of the depth of all of the depressions that are formed in the semiconductor wafer.

A mean value of the depth can also be determined, as an alternative, by the combination of a number of predetermined wetted areas formed on the surface of the semiconductor wafer which, if required, are separated from one another. The individual areas may in this case be wetted successively using a single metering nozzle, or else at the same time using a number of metering nozzles. Where the wetted areas are formed successively, the individual areas should, however, not exhibit any significant difference in the vaporized wetting agent during the time period required for this purpose.

The surface of the semiconductor wafer can optionally be covered with a masking layer away from the area to be measured with the depressions, or away from the areas to be measured. To do this, the wetting agent must not dissolve the masking layer. Furthermore, the masking process on which the masking is based should not leave any residues in the exposed depressions.

Instead of determining the intrinsic weight value of the semiconductor wafer before the recording of the time profile of the decrease in weight and/or before the application of the wetting agent, using the method according to the invention as illustrated in FIG. 1, it is alternatively possible to determine the intrinsic weight value after the recording of the time profile. For both alternatives, the intrinsic weight value and the time profile of the decrease in weight are recorded at relatively close times. This allows the depth to be determined very accurately, since measurement errors which may be caused by drifting of the weighing device used for the weight measurements are avoided.

The method according to the invention is not just suitable for determination of the depth of depressions which have exclusively vertical side walls in a corresponding manner to the depressions 2 illustrated in FIGS. 2 to 4. The method can also be used to determine the depth of depressions whose side walls have different shapes in subareas and, for example, run obliquely or else have recesses or indentations. However, the use of the method is dependent on the length or depth of a subarea of a depression formed from vertical side walls making up the majority of the total depth of the depression, in order that the recorded time profile of the decrease in weight of the semiconductor wafer in phase III of the vaporization process has a considerably pronounced linear section as required for determination of the characteristic weight value. Furthermore, when using depressions such as these for the determination or calculation of the total depth, it is necessary to use that total area which is formed from the areas of the depressions enclosed by these vertical side walls. When using the method for depressions such as these, it may additionally be necessary to carry out a calibration process by means of different methods, such as breaking the semiconductor wafer and measuring the fracture edge using a scanning electron microscope.

In some circumstances, corresponding calibration by means of imaging methods may also be required when there are manufacturing-dependent discrepancies between the depressions. Discrepancies may comprise, for example, irregular features in the essentially vertical side walls or else fluctuations in the areas occupied by the depressions in the surface of the semiconductor wafer.

Figure 6:
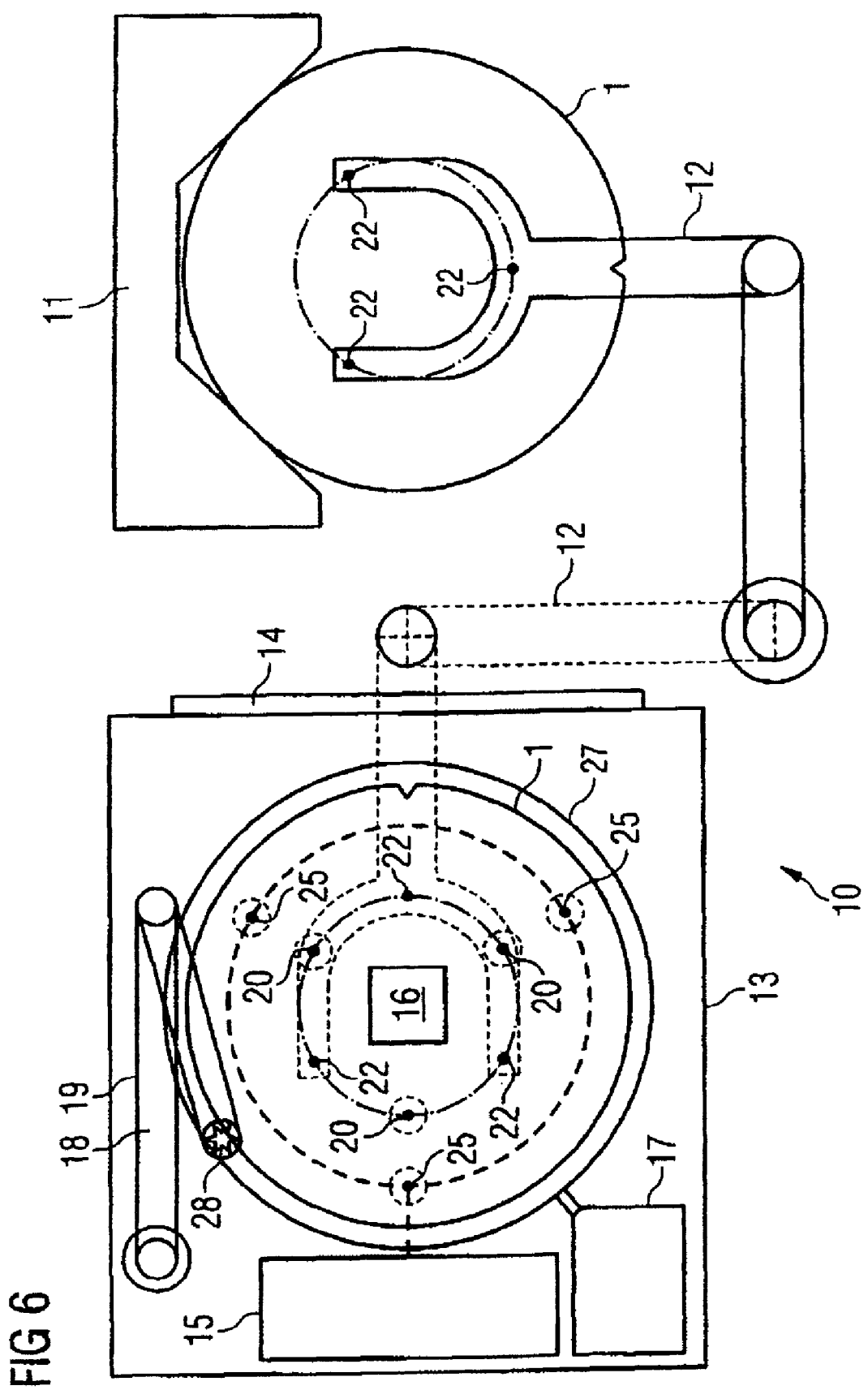
FIG. 6 shows a schematic section illustration of a measurement apparatus according to the invention, from above.

FIG. 6 shows a schematic section illustration of a measurement apparatus 10 according to the invention from above, by means of which the method according to the invention as illustrated in FIG. 1 for determination of the depth of depressions formed in the semiconductor wafer 1 can be carried out. The measurement apparatus 10 has a housing 13 with a weighing device, of which FIG. 6 shows only three contact pins 20 which are arranged in a circle, in order to hold the semiconductor wafer 1. The weighing device by means of which the time profile of the decrease in weight of the semiconductor wafer 1 is recorded during the vaporization process, and by means of which the intrinsic weight value of the semiconductor wafer 1 is determined, is preferably in the form of a comparator scale. A precision scale can optionally also be used.

A robot arm 12 is used to insert the semiconductor wafer 1 (which is held roughly positioned in a holder 11 before the weighing process) into the housing 13 through a sluice 14 arranged on the housing 13. The robot arm 12 also has three contact pins 22 arranged in a circle in order to hold the semiconductor wafer 1.

A positioning device 15 is also arranged in the housing 13, by means of which the semiconductor wafer 1 can be moved accurately into position before being placed on the contact pins 20 of the weighing device. The positioning device 15 has three contact pins 25 which are arranged in a circle and whose height is adjustable, on which the semiconductor wafer 1 can be placed. The positioning device 15 and the contact pins 25 allow the semiconductor wafer 1 to be oriented very precisely on the XY plane within the housing 13, and also to be rotated very accurately through an angle.

The measurement apparatus 10 furthermore has a metering device 18 which is arranged in the housing 13 and has a metering nozzle 28, in order to apply the wetting agent as droplets of a predetermined size to the surface of the semiconductor wafer 1. In order to position the metering nozzle 28 on the surface of the semiconductor wafer, the metering device 18 has a positioning device in the form of a robot arm 19.

An image recording device 16 is also provided in the housing 13 in order to control the positioning of the semiconductor wafer 1 on the contact pins 20 of the weighing device, and the positioning of the metering nozzle 28 on the surface of the semiconductor wafer 1. Furthermore, the image recording device 16 can be used to measure the area of the surface of the semiconductor wafer 1 covered with the wetting agent after the wetting agent has been applied, or else to check it during the vaporization process. For this purpose, the spectral sensitivity of the image recording device 16 is designed to produce high contrast between the wetted surface and the unwetted surface. The image recording device 16 is, for example, in the form of a CCD camera.

A temperature stabilization device 17 with a variable-height temperature transfer plate 27 is provided in the housing 13 in order to raise or lower the semiconductor wafer 1 to a predetermined temperature value before the weighing process. This results in a predetermined vaporization rate of the wetting agent. The transfer plate 27 is provided with a number of cutouts through which the contact pins 20 of the weighing device and the contact pins 25 of the positioning device 15 can be passed.

The measurement apparatus 10 also has an evaluation device, which is not illustrated in FIG. 6. The evaluation device is used to evaluate the recorded time profile of the decrease in weight of the semiconductor wafer 1 during the vaporization of the wetting agent, in order to determine the characteristic weight value of the semiconductor wafer 1. The evaluation device is also used to determine the depth of the depressions from the characteristic weight value, the intrinsic weight value of the semiconductor wafer 1, the density of the wetting agent and the total area occupied by the depressions in the wetted area of the surface of the semiconductor wafer 1. By way of example, the evaluation device may be in the form of a PC with an appropriate evaluation program.

Furthermore, the measurement apparatus 10 may be provided with a sensor device, which is not illustrated in FIG. 6, but is arranged in the housing 13, for recording the concentration of the vaporized wetting agent. This also makes it possible to check the vaporization process.

It is also advantageous to provide further control devices in order to record and to stabilize mechanical oscillations, the pressure and the humidity during the weighing of the semiconductor wafer 1. In addition, the measurement apparatus 10 may be provided with a discharge device for dissipating static charges from the semiconductor wafer 1.

FIGS. 7 to 14 show schematic section illustrations of the measurement apparatus according to the invention in order to explain the process of weighing the semiconductor wafer 1. In order to make the illustration clearer, various level heights within the housing of the measurement apparatus are identified by appropriate lines for an upper level O, a middle level M and a lower level U.

Figure 7:
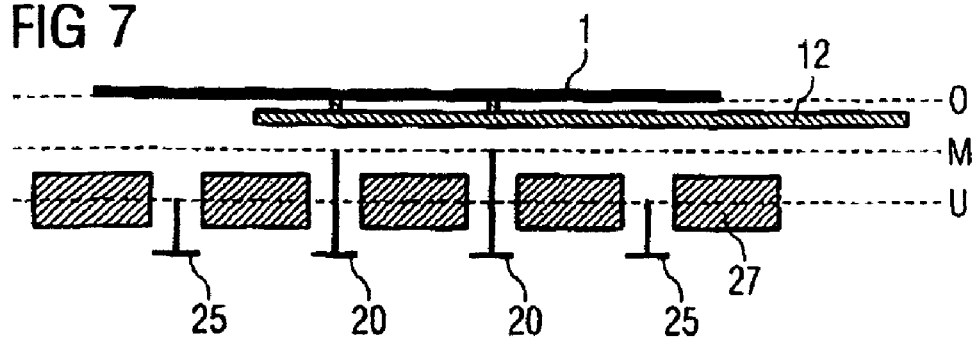
FIGS. 7 to 14 show schematic illustrations of the measurement apparatus according to the invention during a weighing process.
Figure 8:
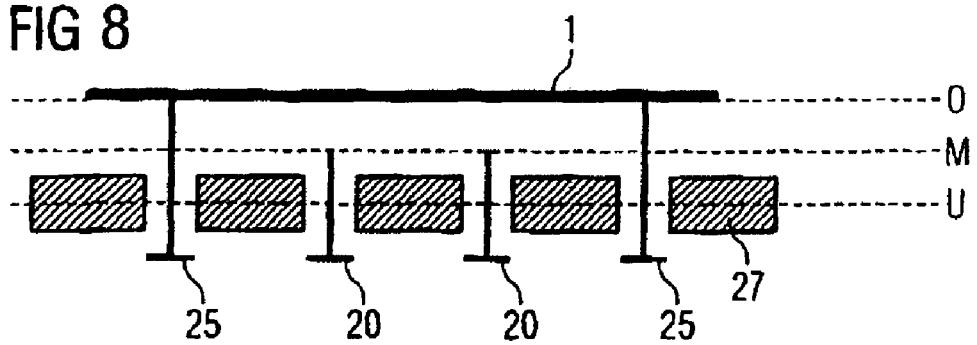

Once the semiconductor wafer 1 has been removed from the holder, the semiconductor wafer 1 is moved into the housing of the measurement apparatus by means of the robot arm 12, as illustrated in FIG. 7. The contact pins 25 which are arranged within the cutouts in the transfer plate 27 are then raised to the upper level O, so that the semiconductor wafer 1 rests on the contact pins 25 as shown in FIG. 8. The robot arm 12 is then once again moved out of the housing, and the semiconductor wafer 1 is positioned precisely by means of the contact pins 25 and using the image recording device. The cutouts in the transfer plate 27 have appropriate dimensions for this purpose in order to allow non-contacting movement of the contact pins 25 within the cutouts.

Figure 9:
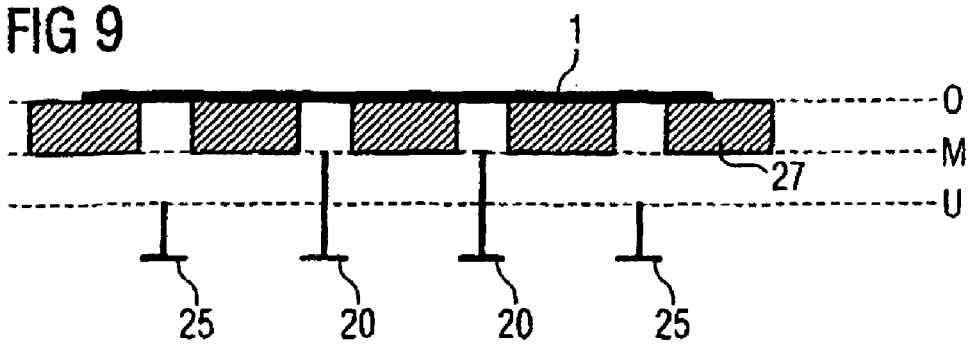
Figure 10:
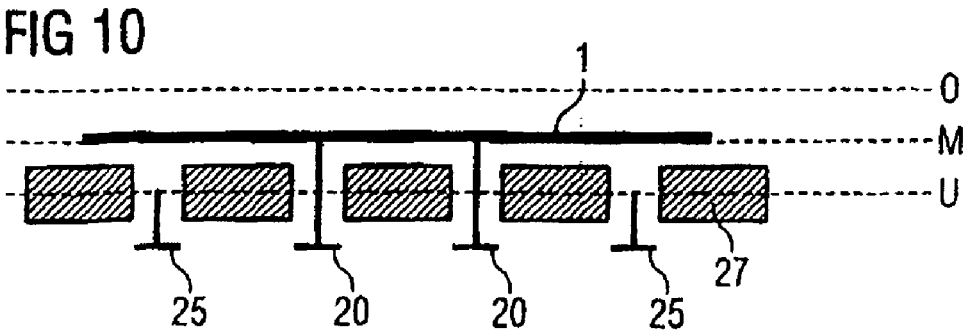

The semiconductor wafer 1 is then placed on the transfer plate 27, as illustrated in FIG. 9, by raising the transfer plate 27 to the upper level O. At the same time, the contact pins 25 of the positioning device are once again lowered to the lower level U. The semiconductor wafer 1 is raised or lowered to the predetermined temperature value by means of the transfer plate 27. Once the semiconductor wafer has reached the predetermined temperature value, the transfer plate 27 is once again lowered to the lower level U, so that the semiconductor wafer 1 comes to rest on the contact pins 20 of the weighing device, as illustrated in FIG. 10. Cutouts of appropriate size are also formed in the transfer plate 27 for the contact pins 20. Once the weighing device has stabilized, the intrinsic weight value of the semiconductor wafer 1 without any wetting agent is measured.

Figure 11:
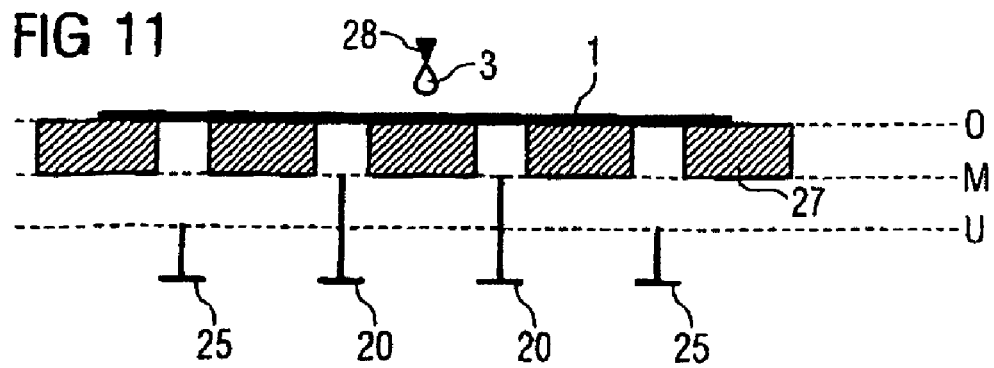
Figure 12:
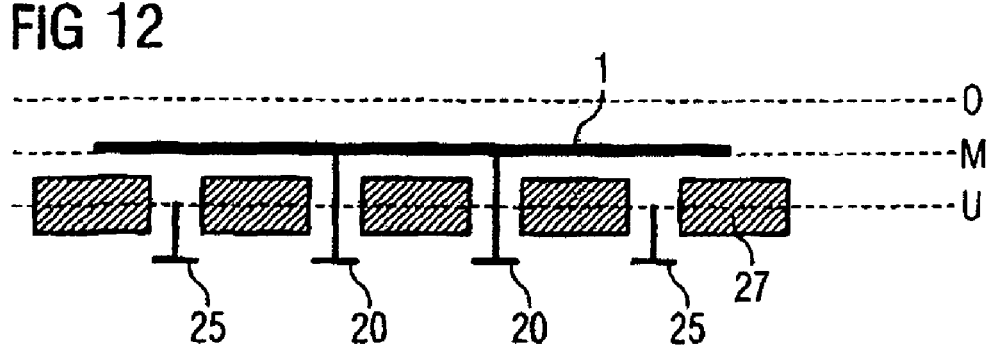

The transfer plate 27 and thus the semiconductor wafer 1 as well are then raised again, as illustrated in FIG. 11, to the upper level. A predetermined droplet of the wetting agent 3 is then applied to a predetermined area of the surface of the semiconductor wafer 1 via the metering nozzle 28 of the metering device, which is positioned with the aid of the image recording device. The semiconductor wafer 1 is then once again placed on the contact pins 20 of the weighing device by lowering the transfer plate 27, as illustrated in FIG. 12. Once the weighing device has stabilized, the weight profile of the semiconductor wafer 1 is measured during the vaporization of the wetting agent. At the same time, the wetted area on the surface of the semiconductor wafer 1 is measured by means of the image recording device and, if required, the concentration of the vaporized wetting agent is measured by means of the appropriate sensor device.

Figure 13:
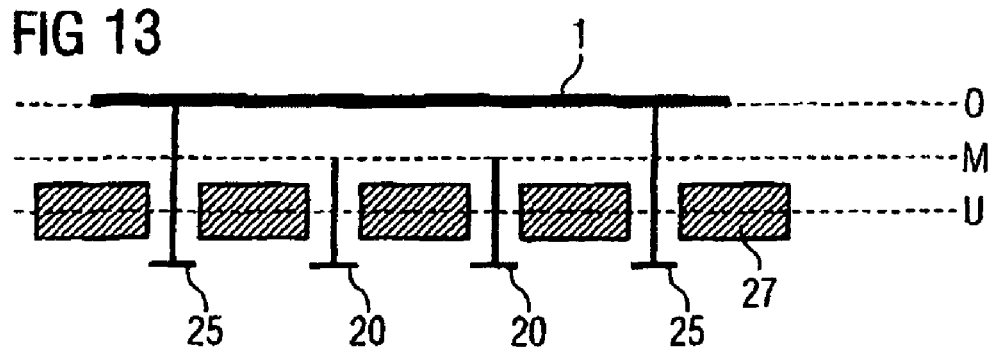
Figure 14:
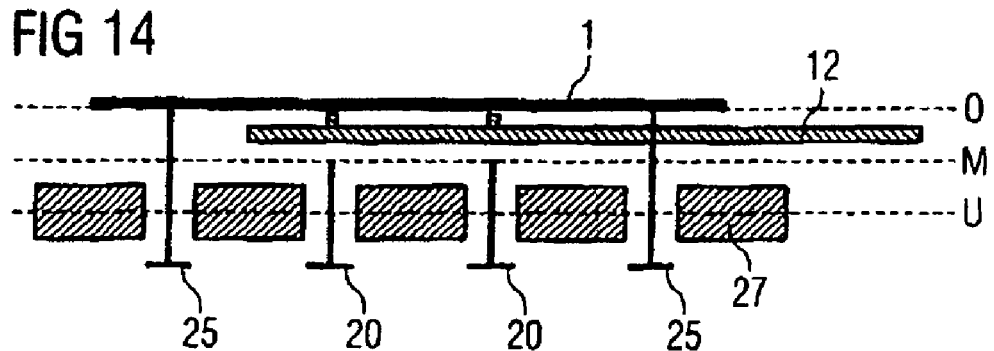

Once the time profile of the decrease in weight of the semiconductor wafer 1 has been recorded, as illustrated in FIG. 13, it is raised to the upper level O by raising the contact pins 25 of the positioning device, and the robot arm 12 is inserted into the housing of the measurement apparatus as illustrated in FIG. 14, in order to withdraw the semiconductor wafer 1 from the housing again.

The method according to the invention and the measurement apparatus according to the invention are not just suitable for determination of the depth of depressions formed in a semiconductor wafer. It is also possible to use the method and the measurement apparatus for determination of the depth of depressions formed in other mount substrates.

LIST OF REFERENCE SYMBOLS

1 Semiconductor wafer
2 Depression
3 Wetting agent
4 Time profile of the decrease in weight
5, 6 Approximate straight lines
7 Intersection
10 Measurement apparatus
11 Holder
12 Robot arm
13 Housing
14 Sluice
15 Positioning device
16 Image recording device
17 Temperature stabilization device
18 Metering device
19 Robot arm
20, 22, 25 Contact pin
27 Transfer plate
28 Metering nozzle
31, 32, 33 Method steps
34, 35 Method steps
R Trench depth
O Upper level
M Middle level
U Lower level

What is claimed is:

1. A method for determination of depth of depressions which are formed in a mount substrate, comprising:
    applying an essentially uniform layer of a wetting agent to an area, which includes depressions, on a surface of the mount substrate;
    recording a time profile of a decrease in weight of the mount substrate during vaporization of the wetting agent;
    evaluating the recorded time profile of the decrease in weight of the mount substrate to determine a characteristic weight value for the mount substrate in a state in which the wetting agent has vaporized from the surface of the mount substrate and the depressions are filled with the wetting agent; and
    determining the depth of the depressions from the characteristic weight value taking into account an intrinsic weight value of the mount substrate without the wetting agent, the density of the wetting agent and a total surface area occupied by the depressions in the area of the surface of the mount substrate.

2. The method as claimed in claim 1, wherein the characteristic weight value of the mount substrate corresponds to an intersection of a first straight line which is defined by a first linear section of the recorded time profile of the decrease in weight of the mount substrate and a second straight line which is defined by a second linear section of the recorded time profile, wherein the first linear section of the recorded time profile corresponds to a state of the mount substrate in which the wetting agent has vaporized from an entire area of the surface of the mount substrate, and the second linear section of the recorded time profile corresponds to a state of the mount substrate in which the wetting agent has vaporized exclusively from the depressions, but the depressions have yet been completely emptied.

3. The method as claimed in claim 1, wherein the wetting agent is applied as drops of a predetermined size to the surface of the mount substrate to form a predetermined circular wetted area.

4. The method as claimed in claim 1, wherein two or more predetermined wetted areas are formed on the surface of the mount substrate.

5. The method as claimed in claim 1, wherein the surface of the mount substrate away from the area to be measured is covered with a masking layer.

6. The method as claimed in claim 1, wherein the wetting agent is applied to an entire surface of the mount substrate, except for a direct edge area.

7. The method as claimed in claim 1, wherein the intrinsic weight value of the mount substrate is determined before or after a recording of the time profile of the decrease in weight of the mount substrate during the vaporization of the wetting agent.

8. The method as claimed in claim 1, wherein the mount substrate is raised to a predetermined temperature value in order to produce a predetermined vaporization rate of the wetting agent.

9. The method as claimed in claim 1, wherein the surface of the mount substrate is cleaned and dried before application of the wetting agent to achieve complete, bubble-free wetting of the surface of the mount substrate and in the depressions.

10. The method as claimed in claim 1, wherein the wetting agent has a defined viscosity and affinity to achieve complete, bubble-free wetting of the surface of the mount substrate and in the depressions.

11. The method as claimed in claim 1, wherein a chemically inert wetting agent is used to avoid chemical reactions between the wetting agent and the mount substrate.

12. The method as claimed in claim 1, wherein an explosion-proof wetting agent is used for the recording of the time profile of the decrease in weight of the mount substrate.

13. An apparatus for determination of depth of depressions which are formed in a mount substrate, comprising:

a metering device for application of an essentially uniform layer of a wetting agent to an area, which includes depressions, on a surface of the mount substrate;

a weighing device for recording a time profile of a decrease in weight of the mount substrate during vaporization of the wetting agent and for determination of an intrinsic weight value of the mount substrate without the wetting agent; and an evaluation device for evaluation of the recorded time profile of the decrease in weight of the mount substrate to determine a characteristic weight value for the mount substrate in a state in which the wetting agent has vaporized from the surface of the mount substrate and the depressions are filled with the wetting agent, and for the determination of the depth of the depressions from the characteristic weight value taking into account the intrinsic weight value of the mount substrate without the wetting agent, the density of the wetting agent and the total surface area occupied by the depressions in an area of the surface of the mount substrate.

14. The apparatus as claimed in claim 13, wherein a positioning device is provided for positioning of the mount substrate on the weighing device.

15. The apparatus as claimed in claim 13, wherein the metering device has a metering nozzle to apply the wetting agent in a form of drops to the surface of the mount substrate.

16. The apparatus as claimed in claim 15, wherein the metering device has a positioning device to position the metering nozzle on the surface of the mount substrate.

17. The apparatus as claimed in claim 16, wherein an image recording device is provided to control the positioning of the mount substrate on the weighing device and the positioning of the metering nozzle on the surface of the mount substrate, and to measure the area of the surface of the mount substrate which is covered with the wetting agent.

18. The apparatus as claimed in claim 13, wherein a temperature stabilization device is provided to raise the mount substrate to a predetermined temperature value.

19. The apparatus as claimed in claim 13, wherein a sensor device is provided for detection of the concentration of the vaporized wetting agent.

20. The apparatus as claimed in claim 13, wherein control devices are provided for detection and stabilization of mechanical oscillations, of pressure and moisture, and a discharge device is provided for dissipating static charges from the mount substrate.

* * * * *